US012629393B2

(12) United States Patent
Noh et al.

(10) Patent No.: US 12,629,393 B2
(45) Date of Patent: May 19, 2026

(54) PHARMACEUTICAL COMPOSITION FOR PREVENTING OR TREATING OSTEOARTHRITIS

(71) Applicants: KOLON LIFE SCIENCE, INC., Seoul (KR); KOLON TISSUEGENE, INC., Rockville, MD (US)

(72) Inventors: Sang Eun Noh, Incheon (KR); Soon Dong Lee, Gyeonggi-do (KR); Hyeon Youl Lee, Gyeonggi-do (KR); Seung Taeh Hwang, Incheon (KR); Ha Eun Kim, Seoul (KR); Min Ho Choi, Seoul (KR)

(73) Assignees: KOLON LIFE SCIENCE, INC., Seoul (KR); KOLON TISSUEGENE, INC., Rockville, MD (US)

( * ) Notice: Subject to any disclaimer, the term of this patent is extended or adjusted under 35 U.S.C. 154(b) by 284 days.

(21) Appl. No.: 16/627,528

(22) PCT Filed: Jun. 29, 2018

(86) PCT No.: PCT/KR2018/007437
§ 371 (c)(1),
(2) Date: Dec. 30, 2019

(87) PCT Pub. No.: WO2019/004794
PCT Pub. Date: Jan. 3, 2019

(65) Prior Publication Data
US 2020/0121726 A1    Apr. 23, 2020

(30) Foreign Application Priority Data
Jun. 30, 2017    (KR) ........................ 10-2017-0083560

(51) Int. Cl.
*A61K 35/32*        (2015.01)
*A61P 19/02*        (2006.01)
*C12N 5/071*        (2010.01)
*C12N 5/077*        (2010.01)

(52) U.S. Cl.
CPC .............. *A61K 35/32* (2013.01); *A61P 19/02* (2018.01); *C12N 5/0655* (2013.01); *C12N 5/0697* (2013.01); *C12N 2501/15* (2013.01); *C12N 2529/00* (2013.01)

(58) Field of Classification Search
None
See application file for complete search history.

(56) References Cited

U.S. PATENT DOCUMENTS

| | | | |
|---|---|---|---|
| 7,005,127 B2 | 2/2006 | Song et al. | |
| 7,282,200 B2 | 10/2007 | Song et al. | |
| 2003/0175257 A1 | 9/2003 | Song et al. | |
| 2004/0171109 A1* | 9/2004 | Haudenschild .... | C07K 14/7155 |
| | | | 435/69.1 |
| 2005/0152882 A1 | 7/2005 | Kizer et al. | |
| 2010/0120149 A1* | 5/2010 | Kim ..................... | C12N 5/0655 |
| | | | 435/396 |
| 2014/0178346 A1* | 6/2014 | Byrne ................ | A61K 38/1875 |
| | | | 424/93.21 |
| 2016/0038544 A1 | 2/2016 | Keller et al. | |

FOREIGN PATENT DOCUMENTS

| | | |
|---|---|---|
| JP | 2009-137980 A | 6/2009 |
| KR | 10-2005-0002898 A | 1/2005 |
| KR | 10-0866101 B1 | 10/2008 |
| KR | 10-2011-0074773 A | 7/2011 |
| KR | 10-2015-0014369 A | 2/2015 |
| KR | 10-1649375 B1 | 8/2016 |
| KR | 10-2017-0073614 A | 6/2017 |
| WO | WO 96/39196 A1 | 12/1996 |
| WO | WO 03/082302 A2 | 10/2003 |
| WO | WO 03/083080 A2 | 10/2003 |
| WO | WO 2016/126139 A1 | 8/2016 |
| WO | WO 2017/075433 A1 | 5/2017 |

OTHER PUBLICATIONS

Phull et al. (2016, http://dx.doi.org/10.1155/2016/1879837, pp. 1-17).*
Gigout et al., 2009, Tissue Engineering Pt A, 15(8): 2237-2248. (Year: 2009).*
Darwin Microfluidics Needle Gauge Table. Accessed at URL: https://darwin-microfluidics.com/blogs/tools/syringe-needle-gauge-table on Oct. 5, 2022. (Year: 2022).*
International Search Report for PCT/KR2018/007437 mailed on Nov. 6, 2018.
Chul-Won Ha et al., "Initial phase I safety of retrovirally transduced human chondrocytes expressing transforming growth factor-beta-1 in degenerative arthritis patients", Cytotherapy, vol. 14, pp. 247-256, 2012 cartilage by cell-mediated gene therapy using transforming growth factor beta vol. 12(14), pp. 1805-1813, 2001 (Abstract is submitted herewith.).
Lee KH et al., "Regeneration of hyaline cartilage by cell-mediated gene therapy using transfo~rming growth factor beta 1-producing fibroblasts.", Hum Gene Ther. vol. 12(14), pp. 1805-1813, 2001 (Abstract is submitted herewith.).
Sun U. Song et al., "Hyaline Cartilage Regeneration Using Mixed Human Chondrocytes and Transforming Growth Factor-$\beta$1-Producing Chondrocytes", Tissue Engineering, vol. 11, 2005 (Abstract is submitted herewith.).

(Continued)

*Primary Examiner* — Allison M Fox
(74) *Attorney, Agent, or Firm* — The PL Law Croup, PLLC.

(57) ABSTRACT

A pharmaceutical composition for prevention or treatment of osteoarthritis according to an embodiment of the present disclosure includes cells or cell groups having a specific size or less. Mixed cells, which are selected to a specific size or less as an active ingredient of the present invention, of transformed mammalian cells with TGF-$\beta$ and untransformed mammalian cells minimize aggregation between chondrocytes and have beneficial therapeutic effects. In addition, when administering the selected mixed cells having the specific size or less to a patient, patient compliance may be improved, and it is easy to manage quality in therapeutic agent manufacturing facilities or hospitals.

16 Claims, 4 Drawing Sheets

(56) References Cited

OTHER PUBLICATIONS

Office action issued on Sep. 1, 2020 from Intellectual Property Office of Singapore in a counterpart Singapore Patent Application No. 11201913808S (all the cited references are listed in this IDS.).

Certificate of Analysis "Short Tandem Repeat (STR) DNA Amplification and Analysis", www. bioreliance.com.

Hytham S. Salem, et al. "The Safety and Efficacy of a Novel Cell-Based Gene Therapy for Knee Osteoarthritis" Orthopaedic Surgery, Surgical Technology International vol. 35, pp. 1-7.

Search Report issued on Jun. 29, 2018 from Singapore Patent Office in a counterpart Singapore Patent Application No. 11201913808S.

Ha C. W. et al., "Initial phase I safety of retrovirally transduced human chondrocytes expressing transforming growth factor-beta-1 in degenerative arthritis patients", Cytotherapy, Feb. 1, 2012, pp. 247-256, vol. 14, No. 2.

Search Report issued on Jun. 28, 2021 from Singapore Patent Office in a counterpart Singapore Patent Application No. 11201913793S.

Chul-Won Ha et al., "Initial phase I safety of retrovirally transduced human hondrocytes expressing transforming growth factor-beta-1 in degenerative arthritis patients", Cytotherapy, Feb. 29, 2012, pp. 247-256, vol. 2012, No. 14.

Cherian J. J. et al., "Preliminary results of a phase II randomized study to determine the efficacy and safety of genetically engineered allogeneic human chondrocytes expressing TGF-B1 in patients with grade 3 chronic degenerative joint disease of the knee", Osteoarthr. Cartil., Jul. 16, 2015, pp. 2109-2118, vol. 23, No. 2015, Osteoarthritis Research Society International.

I-Ming Jou et al., "Thrombospondin 1 as an Effective Gene Therapeutic Strategy in Collagen-Induced Arthritis", Arthritis & Rheumatism, vol. 52, No. 1, pp. 339-344, 2005.

MFDS News, KFDA revokes KOLON Life Science's Invossa-K Inj, Ministry of Food and Drug Safety (MFDS), published May 25, 2019 (English translation of summary thereof is submitted herewith).

Korea Health Industry Development Institute, "Development of Invossa, degerative arthritis medicine, and follow-up pipeline", Final Evaluation Report of High-Tech Biopharmaceuticals Project for Global Market, Attachment 3 at p. 13, Jul. 2019 (Translation of Attachment 3 is submitted herewith).

Office action issued on Dec. 27, 2019 from Korean Patent Office in a counterpart Korean Patent Application No. 10-2018-0075978 (all the cited references are listed in this IDS.).

Office action issued on Aug. 2, 2022 from Japan Intellectual Property Office in a counterpart Japanese Patent Application No. 2020-522653 (all the cited references are listed in this IDS.) (English translation is also submitted herewith.).

Examination report on Mar. 1, 2021 from IP Australia Office in a counterpart Australian Patent Application No. 2018290628.(all the cited references are listed in this IDS.).

J.J. Cherian et al. "Preliminary results of a phase II randomized study to determine the efficacy and safety of genetically engineered allogenic human chondrocytes expressing TGF-$\beta$1 in patients with grade 3 chronic degenerative joint disease of the knee", Osteoarthritis and Cartilage, 2015, vol. 23, No. 12, pp. 2109-2118.

European Search Report For EP18824811.6 issued on Feb. 17, 2021 from European patent office in a counterpart European patent application.(all the cited references are listed in this IDS.).

Barsov Eugene V. "Immortalization of Human and Rhesus Macaque Primary Antigen-Specific T Cells by Retrovirally Transduced Telomerase Reverse Transcriptase", Current Protocols in Immunology, Nov. 1, 2011, vol. 95, No. 1.

L.S. Moreira Teixeira et al. "High throughput generated micro-aggregates of chondrocytes stimulate cartilage formation in vitro and in vivo", European Cells and Materials, Jun. 5, 2012, vol. 23, P387-399.

* cited by examiner

Before cell strainer                After cell strainer

Before cell strainer          After cell strainer

Before cell strainer          After cell strainer

PHARMACEUTICAL COMPOSITION FOR PREVENTING OR TREATING OSTEOARTHRITIS

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2018/007437, filed Jun. 29, 2018, which claims priority to the benefit of Korean Patent Application Nos. 10-2017-0083560 filed on Jun. 30, 2017 and 10-2018-0075947 filed on Jun. 29, 2018 in the Korean Intellectual Property Office, the entire contents of which are incorporated herein by reference.

BACKGROUND

1. Technical Field

The present invention relates to a pharmaceutical composition for prevention or treatment of osteoarthritis and a manufacturing method.

2. Background Art

Osteoarthritis, also called degenerative arthritis, is a chronic disease that causes a damage to joint cartilage, underlying bone and ligaments, and inflammation and pain due to cartilage damage or degenerative changes. The osteoarthritis occurs in almost all joints in the body, including fingers, knees (knee joints, patella), hips (hip joints, coxa), backs (lumbar joints), and neck (cervical joints). It has been thought that the osteoarthritis is associated with age in a view of an occurrence thereof, and is caused by overuse of the joints and cartilage wear due to aging. However, as a mechanism for occurrence of the osteoarthritis and responses to diverse stimuli of chondrocytes have recently disclosed, it has been understood that the osteoarthritis is not an inevitable phenomenon associated with aging but is a joint damage due to different causes such as abnormality of chondrocyte metabolism balance or the like, as well as a joint disease caused by interaction between different systemic and/or local factors due to the above joint damage.

Major symptoms of the osteoarthritis include repeated pains, joint stiffness, reduced mobility and a loss of function. In general, the symptoms progress gradually over years. As the disease progresses to some extent, a surface of the joint becomes irregular due to the loss and degeneration of articular cartilage, thereby causing an increase in a degree of pain, and progressive movement disorder may lead to significant disruption to daily life. Further, joint deformation may also be caused.

Currently, studies to target modulators and biochemical factors associated with cartilage growth are underway. These factors include, for example, bone morphogenic protein (BMP), which is an effective stimulant of bone formation, and a transforming growth factor beta (TGF-β), which stimulates cell growth and extracellular matrix (ECM) formation.

In particular, the TGF-β is known to be involved in proteoglycan synthesis, chondrocyte growth and tissue regeneration. Further, the TGF-β is also known to have immunosuppressive and anti-inflammatory functions. Indeed, other growth factors such as epidermal growth factor (EGF), insulin-like growth factor I (IGF-I), and basic fibroblast growth factor (bFGF) also stimulate cartilage regeneration, but these growth factors have no effect on cartilage damage.

Such growth factors as described above entail difficulties in determining a concentration, release rate, delivery method, or the like at the time of administration. The researchers have continued to make efforts to deliver these factors through liposomes or by dissolving in a medium, based on the results proved in animal experiments. However, application of these factors to a human being has yet to be greatly improved.

The use of genetically modified chondrocytes is a novel technique that has successfully established cartilage regeneration in combination with cell-mediated gene therapy (Lee K H et al., Hum Gene Ther 2001; 12: 1805-1813, SUN U. SONG et al. Tissue Engineering 2005; 11: 1516-1526). This method uses a combination of allogeneic human chondrocytes transduced by a retroviral vector having TGF-β gene and allogeneic normal chondrocytes. This method can induce cartilage regeneration while minimizing surgical procedures.

Mature chondrocytes have a spherical shape, and may synthesize Type II collagen fibers and condensed proteoglycan and non-collagenous fibers having very high molecular weight.

Efforts to transplant chondrocytes in osteoarthritis have been continuously made in order to treat the damaged joint. In particular, techniques to apply chondrocytes as a tissue engineering support for cartilage damage have been disclosed. For instance, Korean Patent Laid-Open Publication No. 10-2015-0014369 discloses a technique for production of a bead-shaped chondrocyte therapeutic agent, including inoculating chondrocytes or cell with chondrogenic differentiation capability in a V-shaped deep well plate, centrifuging and culturing in a three-dimension culture. The above document describes that, since the cartilage damaged area is filled with the bead-shaped chondrocytes, a defect site may be repaired regardless of the shape and thickness of the cartilage damaged area.

In addition, U.S. Patent Application Publication No. 2005-0152882 describes a composition for promoting growth of cartilage, which includes a combination of a matrix and cartilages in a form of particles having a particle diameter of 1 to 27 mm.

Further, U.S. Patent Application Publication No. 2016-0038544 discloses formation of a high density chondroblast population to produce cartilage-like tissues for replacing the cartilage in osteoarthritis.

As described above, in a case of known therapeutic compositions using chondrocytes, it was common to use aggregates such as small-sized tissues or high-density populations, whereas therapeutic effects of the chondrocyte compositions without tissues or cell mass are still unknown. Meanwhile, a small difference may bring or make completely different results in case of biological products. In fact, it has not been demonstrated that chondrocytes not forming aggregates may have therapeutic effects.

In addition, there remains a need for identifying and selecting cells with regard to what size and type of cells are required, so as to provide a cell therapeutic agent with ensured effectiveness (i.e., therapeutic efficacy) at a level practically applicable to a patient.

SUMMARY

Under these circumstances, the present inventors have made efforts to develop a cell therapeutic agent for specific diseases, in particular, osteoarthritis. As a result, the present inventors have found that selection of cells having specific sizes, for example, transformed cells so as to express a target gene, for example, TGF-β, and untransformed normal cells, respectively, may minimize aggregation between chondrocytes, while having effective therapeutic effects.

In addition, the present inventors have found that, when mixed cells having a selected specific size or smaller are administered to a patient, patient compliance may be improved while maintaining excellent therapeutic effects, and the mixed cells enable easy to quality control in therapeutic agent manufacturing facilities or hospitals for administration to patients actually. On the basis of the finding, the present invention has been completed.

Accordingly, an object of the present invention is to provide a pharmaceutical composition for prevention or treatment of osteoarthritis.

In addition, another object of the present invention is to provide a kit for preparation of a cell therapeutic agent.

Further, another object of the present invention is to provide a method for manufacturing a therapeutic agent for osteoarthritis.

Hereinafter, the present invention will be described in more detail.

According to one aspect of the present invention, there is provided a pharmaceutical composition for prevention or treatment of osteoarthritis, which includes transformed mammalian cell population, wherein cells or cell groups included in the population have a particle diameter $D_{90}$ of less than 200 μm.

The most important characteristic of the present invention is to establish a criterion for specifying transformed mammalian cells (cell groups or cell population) with a target gene [for example, TGF-β1 among TGF-βs], and is to use the transformed mammalian cells as a cell therapeutic composition by selecting the cells under the criterion based on a particle size, e.g., the particle diameter $D_{90}$ of less than 200 μm, and identifying effectiveness of the cells.

The term "transformation" used herein is synonymous with and interchangeably used with transduction or transfection.

The cells or cell groups included in the mammalian cell population are an active ingredient of the inventive composition and are defined as a single cell or a combined form of cells.

In the present invention, the classification criterion of the cells or cell groups included in the mammalian cell population is a particle size, in particular, $D_x$ of a particle diameter distribution.

In the present disclosure, the term "$D_x$ of a particle diameter distribution", which is used to mention the criterion for the mammalian cell population, represents $x^{th}$ percentile of the distribution, and in the present invention, for example, $D_{90}$ represents $90^{th}$ percentile. In a case of $D_{90}$, this may often be recorded as D (0.90), D [0.9] or in a similar way. With respect to a median particle size and $D_x$, a capital letter 'D' or a small letter 'd' may be interchangeable and have the same meaning as each other.

The cells or cell groups included in the transformed mammalian cell population preferably have a particle diameter $D_{90}$ of less than 200 μm. The particle diameter of the cells or cell groups included in the transformed mammalian cell population may range, for example, from 1 to 199 μm, from 1 to 150 μm, from 1 to 100 μm, from 1 to 90 μm, from 1 to 80 μm, from 1 to 70 μm, from 1 to 60 μm, from 1 to 50 μm, or from 1 to 40 μm.

Meanwhile, in a case of the transformed mammalian cell population having a particle diameter $D_{90}$ of more than 200 μm, irregular and large aggregates do not disappear but remain, which are not suitable for application to a pharmaceutical composition for treatment of osteoarthritis.

In the present invention, a cell or cell group included in the transformed mammalian cell population is preferably a cell or cell group expressing TGF-β, and most preferably a cell or cell group expressing TGF-β1. According to the present invention, the cell population is preferably inactivated.

The inactivation may be performed by irradiation, wherein the irradiation includes a gamma-ray, x-ray or electron ray.

Further, according to a preferred embodiment of the present invention, the cell population may be mixed with untransformed mammalian cell population and then administered.

The cells or cell groups included in the untransformed mammalian cell population preferably have a particle diameter $D_{90}$ of less than 300 μm. More particularly, the cells or cell groups included in the untransformed mammalian cell population preferably may have a particle diameter $D_{90}$, for example, in a range of 1 to 299 μm, 1 to 240 μm, 1 to 230 μm, 1 to 220 μm, 1 to 210 μm, 1 to 200 μm, 1 to 190 μm, 1 to 180 μm, 1 to 170 μm, 1 to 160 μm, 1 to 150 μm, 1 to 140 μm, 1 to 130 μm, 1 to 120 μm, 1 to 110 μm, 1 to 100 μm, 1 to 90 μm, 1 to 80 μm, 1 to 70 μm, 1 to 60 μm, 1 to 50 μm, or 1 to 40 μm.

On the other hand, in a case of the untransformed mammalian cell population having a particle diameter $D_{90}$ of 300 μm or more, irregular and large aggregates may still remain without disappearance, hence being undesirable for application to a pharmaceutical composition for treatment of osteoarthritis.

In one embodiment of the present invention, it was found that the transformed cells so as to express TGF-β and the untransformed mammalian cells are advantageously separated to have different specific sizes, respectively, in order to minimize aggregation between chondrocytes and achieve beneficial therapeutic effects. Further, when some selected cells having a specific size or less are administered to a patient, patient compliance may be improved, and it is easy to manage quality in therapeutic agent manufacturing facilities or hospitals.

Further, according to one embodiment, it was confirmed that screening chondrocytes, which express TGF-β, as well as untransformed mammalian cells, that is, normal cells through filtration or other methods so as to obtain cells or cell groups having a specific size may inhibit aggregates between cells ('intercellular aggregates').

In other words, if $D_{90}$ value of cells or cell groups included in the transformed mammalian cell population is less than 200 μm, e.g., exactly 100 μm, while $D_{90}$ value of cells or cell groups included in the untransformed mammalian cell population is less than 300 μm, for example, 200 μm, intercellular aggregates may be effectively inhibited.

Further, the cells or cell groups with the specific size may be in a single cell state, a colony state, a cluster state or a mixture thereof.

According to a preferred embodiment of the present invention, a ratio of the untransformed mammalian cell population to the transformed mammalian cell population may range from 0.1 to 10:1, preferably from 1 to 10:1, more preferably from 1 to 3:1, and most preferably 3:1, based on the number of cells.

In the present invention, the mammalian cell may be a chondrocyte or chondroprogenitor cell.

As used herein, the term "chondrocyte" refers to a discrete chondrocyte population regardless of whether the cell is de-differentiated or re-differentiated. After several hours of in vitro culture, it was observed that the chondrocytes are de-differentiated into other cell types such as fibroblasts. However, when performing induction, these cells may be re-differentiated into chondrocytes. For the purposes of the present invention, the "chondrocyte" refers to a sample including original start-up chondrocyte culture, optionally containing chondrocytes which are differentiated over time.

In the present invention, the chondrocytes are preferably allogenic cells. It will be appreciated that the present invention may also be practiced with not only single cells but also mixed culture of connective tissue cells. It will be appreciated that the connective tissue cells may be treated with a compound or radioactively to allow the cells to stably express the gene of interest, preferably, TGF-β. Preferably, the connective tissue cells do not occur an immune response to a host organism injected with the cells. In this regard, in a case of cell-mediated gene treatment or somatic cell treatment, allogeneic cells as well as autologous cells may be used.

Further, the mammalian cells may be derived from a human being.

As used herein, the term "prevention" refers to inhibiting development of a disease or disorder in an animal, such as a mammal, that has never been diagnosed as having a disease or disorder, but is subject to such a disease or disorder.

As used herein, the term "treatment" means (i) inhibiting development of a disease or disorder; (ii) alleviation of the disease or disorder; and (iii) removal of the disease or disorder, preferably the disease or disorder to be treated is osteoarthritis.

In addition, the composition of the present invention may further include a pharmaceutically acceptable carrier.

The pharmaceutically acceptable carriers included in the pharmaceutical composition of the present invention are those conventionally used in a formulation, which include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrups, methylcellulose, methylhydroxybenzoate, propylhydroxybenzoate, talc, magnesium stearate and mineral oil, but it is not limited thereto. The pharmaceutical composition of the present invention may further include a lubricant, a wetting agent, a sweetening agent, a flavoring agent, an emulsifying agent, a suspending agent, a preservative, etc. in addition to the above components, but it is not limited thereto. Desired pharmaceutically acceptable carriers and formulations are described in detail in Remington's Pharmaceutical Sciences (19th ed., 1995).

An appropriate dosage of the pharmaceutical composition of the present invention may vary and prescribed depending on factors such as a formulation method, administration method, age, body weight, gender, pathological condition, food, administration time, route of administration, excretion rate and responsiveness of the patient.

Meanwhile, the dosage of the pharmaceutical composition of the present invention is preferably $1.0 \times 10^6$ to $3 \times 10^7$ cells per time.

The pharmaceutical composition of the present invention may be administered parenterally, and when parenterally administering, may be administered through intraarticular, intravenous, subcutaneous, intramuscular, intraperitoneal injection or transdermal route. Preferably, the pharmaceutical composition of the present invention may be injected into a joint cavity region. With respect to the pharmaceutical composition of the present invention, administration routes are preferably determined depending on types of diseases to which the inventive composition is applied.

A concentration of the active ingredient contained in the composition according to the present invention may be determined in consideration of the purpose of treatment, condition of a patient, period of time required, severity of a disease, and the like.

The pharmaceutical composition of the present invention may be formulated into a unit dosage form using a pharmaceutically acceptable carrier and/or excipient according to a method easily implemented by those having ordinary skill in the art to which the present invention pertains ('those skilled in the art'), otherwise, by introducing the composition into a multi-dose container. In this case, the formulation may be in the form of solutions, suspensions or emulsions in oils or aqueous media or in the form of excipients, powders, granules, tablets or capsules, and may additionally contain dispersing or stabilizing agents.

According to another aspect of the present invention, there is also provided a kit for preparation of a cell therapeutic agent for treating or preventing osteoarthritis, which includes a mammalian cell population transformed with TGF-β, wherein cells or cell groups included in the population preferably have a particle diameter $D_{90}$ of less than 200 μm.

The kit may further include an untransformed mammalian cell population, wherein cells or cell groups included in the untransformed mammalian cell population preferably have a particle diameter $D_{90}$ of less than 300 μm.

The kit may include not only the mammalian cell population as a cell therapeutic agent but also a tool, a reagent and the like commonly used in the art.

Examples of the tool or reagent include suitable carriers, markers capable of generating detectable signals, chromophores, solubilizing agents, cleaning agents, buffers, stabilizers, and the like, but it is not limited thereto. When the marker is an enzyme, a substrate capable of measuring enzyme activity and a reaction terminator may be included. The carriers may include a soluble carrier and an insoluble carrier, and the soluble carrier may include, for example, a physiologically acceptable carrier known in the related art, for example, PBS. Further, the insoluble carrier may include, for example, polystyrene, polyethylene, polypropylene, polyester, polyacrylonitrile, fluorine resin, cross-linked dextran, polysaccharide, polymer such as magnetic fine particles plated with metal on latex, other substances such as paper, glass, metal, agarose and a combination thereof.

According to another aspect of the present invention, there is provided a method for manufacturing a therapeutic agent for osteoarthritis, including steps of:

(1) preparing a transformed mammalian cell population with TGF-β and an untransformed mammalian cell population, respectively;

(2) selecting cells or cell groups having a particle diameter $D_{90}$ of less than 200 μm included in the mammalian cell population transformed with TGF-β in the above step (1); and cells or cell groups having a particle diameter $D_{90}$ of less than 300 μm included in the untransformed mammalian cell population, respectively;

(3) filling a separate vial with both of the selected cell populations in step (2), respectively; and

(4) mixing the selected cell populations in the vial in step (3).

That is, with regard to the therapeutic agent for osteoarthritis, the mammalian cell population transformed with TGF-β and the untransformed mammalian cell population may be mixed and then administered. Further, the cell or cell group included in the transformed mammalian cell population with TGF-β may have a particle diameter $D_{90}$ of less than 200 μm while the cell or cell group included in the untransformed mammalian cell population preferably has a particle diameter $D_{90}$ of less than 300 μm.

The selection as described above may be physical, chemical or electronic selecting. As a physical selecting method, a mesh having a predetermined size or use of a cell strainer or a filter may be applied. In addition to such physical selecting, a cell selecting process using fluorescence, magnetic properties and/or electric charge of cells may be applied without limitation thereof.

Since the kit and the method for manufacturing a therapeutic agent of the present invention include the above-described configurations, redundant contents will not be described in order to avoid excessive complexity of the present disclosure.

The mixed cell-based composition including the selected mammalian cells having a specific size or less transformed with TGF-β as well as untransformed mammalian cells as active ingredients of the composition according to the present invention exhibits excellent therapeutic effects without including cell masses, that is, aggregates, and therefore, can be easily distinguished from foreign substances in an aspect of pharmaceutical quality control, thereby achieving advantages of easy management in therapeutic agent manufacturing facilities or hospitals. In addition, the selected cells do not exhibit additional aggregation between chondrocytes, thereby it is beneficial for storage. Furthermore, when administering the selected mixed cells having the specific size or less to a patient, patient compliance may be improved.

BRIEF DESCRIPTION OF THE DRAWINGS

FIG. 5 is photographs illustrating results of H & E staining analysis of cartilage tissues when treating the MIA-induced osteoarthritis animal model with the selected mixed cells.

DETAILED DESCRIPTION

Figure 1:
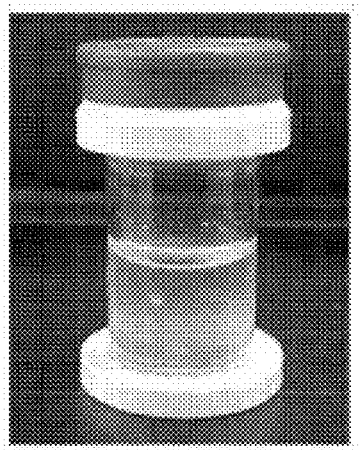
FIG. 1 is views illustrating vials before and after chondrocytes passed through a cell strainer.
Figure 1:
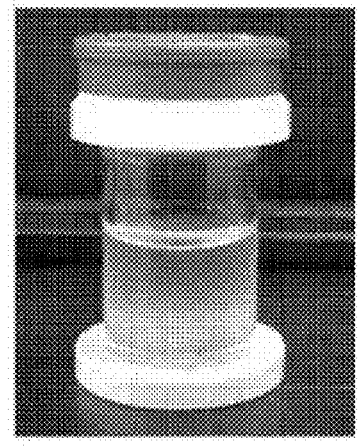

Hereinafter, the following embodiments are provided to more concretely describe the present invention. It will be apparent to those skilled in the art that the scope of the present invention in regard to the objects of invention is not limited by these embodiments.

Example 1. Preparation of Cell Therapeutic Agent

The cell therapeutic agent used in this example of the present invention is a transformed cell population so as to express TGF-β1 (NCBI Reference Sequence: NM_000660.6) (first population; hereinafter referred to as TC) and a normal cell population without transformation using the above gene (second population; hereinafter referred to as HC).

The TC could be prepared by injecting cDNA of TGF-β1 into cells according to a known method. For instance, the cDNA of TGF-β1 is inserted into a known vector having a resistant gene such as ampicillin or neomycin (for example, pCI (containing ampicillin resistant gene) from Promega Co.) to construct a vector containing cDNA of TGF-β1, followed by injecting the same into chondrocytes according to a known method such as a calcium phosphate method or a lipofectin method, thus to prepare TC. Otherwise, the TC may be prepared using a gene delivery vehicle such as retroviral vectors, lentiviral vectors, and the like.

The HC and TC are human-derived chondrocytes, wherein HC is a normal chondrocyte while TC is a transformed chondrocyte to secrete TGF-β1. A method for construction of HC and TC has been disclosed in known documents [Cytotherapy, 2012 February; 14 (2): 247-256) and U.S. Pat. Nos. 7,005,127 and 7,282,200.

A mixing ratio of HC and TC was 3:1 based on the number of cells and was applied to the following examples.

The prepared TC and HC were filled in a vial, respectively, then frozen and prepared/stored for use as a mixed cell-based therapeutic agent. At this time, the TC was inactivated by irradiation before or after freezing.

Example 2. Selection of Cell Types Having Efficiency

The present inventors have intended to identify effectiveness of the mixed cell, which is the cell therapeutic agent prepared in Example 1, according to the cell aggregates type and size.

For this purpose, a cell strainer was prepared for each pore size, and then subjected to a series of quality control (QC) for determining whether HC cells and TC cells were aggregated.

2-1. Identification of Cell Aggregation in HC Cells Depending Upon the Pore Size of Cell Strainer The present inventors have cultured HC cells and collect a cell suspension. Some of the cells were not filtered using a cell strainer, and the cells were filled in a vial and inspected for foreign substance. The remaining cell suspension was sieved with cell strainers having pore sizes of 200 and 300 μm, respectively, followed by inspection of foreign substances after cell filtration using the cell strainers.

The results are shown in Table 1 below.

TABLE 1

| HC cell | Non-use of cell strainer | 200 μm | 300 μm |
|---|---|---|---|
| Cell aggregation after using a cell strainer | Yes | No | Yes |

That is, in order to determine whether or not the cell aggregation phenomenon of HC cells depending upon the pore size of the cell strainer, after passing the cell suspension through the cell strainer to completely remove cell aggregates, whether or not the cell aggregate was reduced has been checked. For the HC cells, the cells passing through 200 μm cell strainer were all filtered out of the cell aggregate as shown in FIG. 1, and therefore, were passed for foreign substance inspection after filling.

Figure 2A:
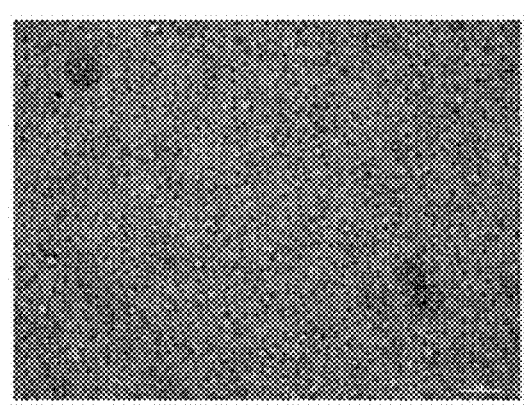
FIG. 2A is photographs illustrating microscopic observation results before and after untransformed cells passed through the cell strainer.
Figure 2A:
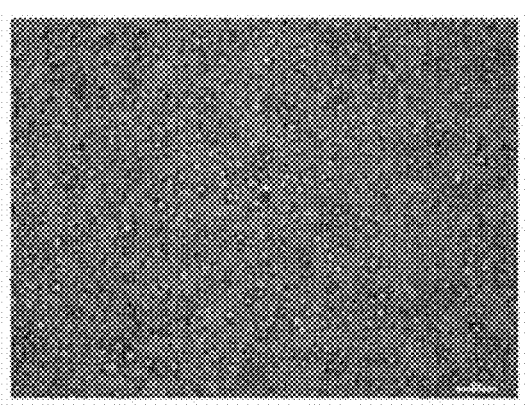

Further, as shown in FIG. 2A, it was observed under a microscope that the cell aggregate disappeared after application of 200 μm cell strainer.

On the other hand, after application of 300 μm cell strainer, it was visibly confirmed that irregular and large aggregate as shown in FIG. 1 were not removed but remained.

Accordingly, in a case of HC cell, it could be seen that cells having a particle diameter $D_{90}$ of less than 300 μm, which can pass through the 300 μm cell strainer, in particular, cells having a particle diameter $D_{90}$ of less than 200 μm are preferable.

2-2. Identification of Cell Aggregation in TC Cells Depending Upon the Pore Size of Cell Strainer The present inventors have cultured TC cells and collect a cell suspension. Some of the cells were not filtered using a cell strainer, and the cells were charged in a vial and inspected for foreign substance. The remaining cell suspension was sieved with cell strainers having pore sizes of 70, 100 and 200 μm, respectively, followed by inspection of foreign substance after cell filtration using the cell strainers.

The results are shown in Table 2 below.

TABLE 2

| TC cell | Non-use of cell strainer | 70 μm | 100 μm | 200 μm |
|---|---|---|---|---|
| Cell aggregation after using a cell strainer | Yes | No | No | Yes |

That is, in order to determine whether or not the cell aggregation phenomenon of TC cells depending upon the pore size of the cell strainer, after passing the cell suspension through the cell strainer to completely remove cell aggregation, whether or not the cell aggregation was reduced has been checked. For TC cells, the cells passing through 70 μm and 200 μm cell strainers were all filtered out of the cell aggregate as shown in FIG. 1, and therefore, were passed for foreign substance inspection after filling.

Figure 2B:
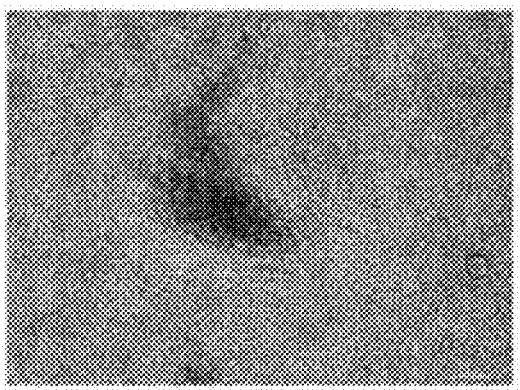
FIG. 2B is photographs illustrating microscopic observation results before and after transformed cells passed through the cell strainer.
Figure 2B:
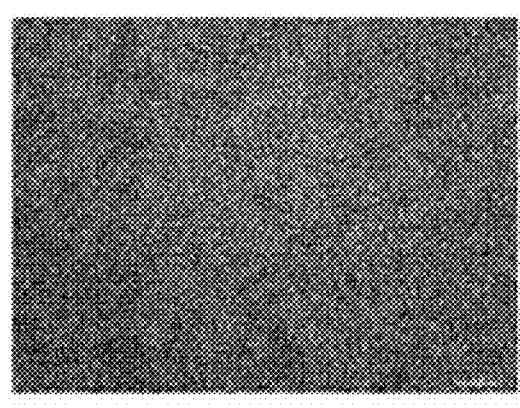

Further, as shown in FIG. 2B, it was observed under a microscope that the cell aggregate disappeared after application of 100 μm cell strainer.

On the other hand, after application of 200 μm cell strainer, it was visibly confirmed that irregular and large aggregate shown in FIG. 1 were not removed but remained.

Accordingly, in a case of TC cell, it could be seen that cells having a particle diameter $D_{90}$ of less than 200 μm, which can pass through the 200 μm cell strainer, in particular, cells having a particle diameter $D_{90}$ of less than 100 μm are preferable.

Example 3. Identification of Further Aggregation Prevention after Application of Cell Strainer The present inventors have determined whether or not the cells before and after passing through the cell strainer prepared in Example 2 have a change in cell aggregation type and size over time, and whether or not the application of the strainer has been helpful to prevent further aggregation.

For this purpose, a cell strainer was prepared for each pore size and used for filtration. Then, the vial was left at room temperature to determine whether or not the aggregation of HC and TC cells was changed over time.

3-1. Identification of Cell Aggregation in HC Cells Over Time after Application of Cell Strainer The present inventors have cultured HC cells and collect a cell suspension. Some cells were filled in a vial without application of a cell strainer and observed cell aggregation over time. The remaining cell suspension was sieved with a cell strainer having a pore size of 200 μm and the cells were filled in the vial, followed by determining cell aggregation phenomenon over time.

In order to determine whether or not the cell aggregation phenomenon of HC cells depending upon the pore size of the cell strainer, after passing the cell suspension through the cell strainer to completely remove cell aggregates, whether or not the cell aggregate was reduced has been checked.

Figures 3A, 3B:
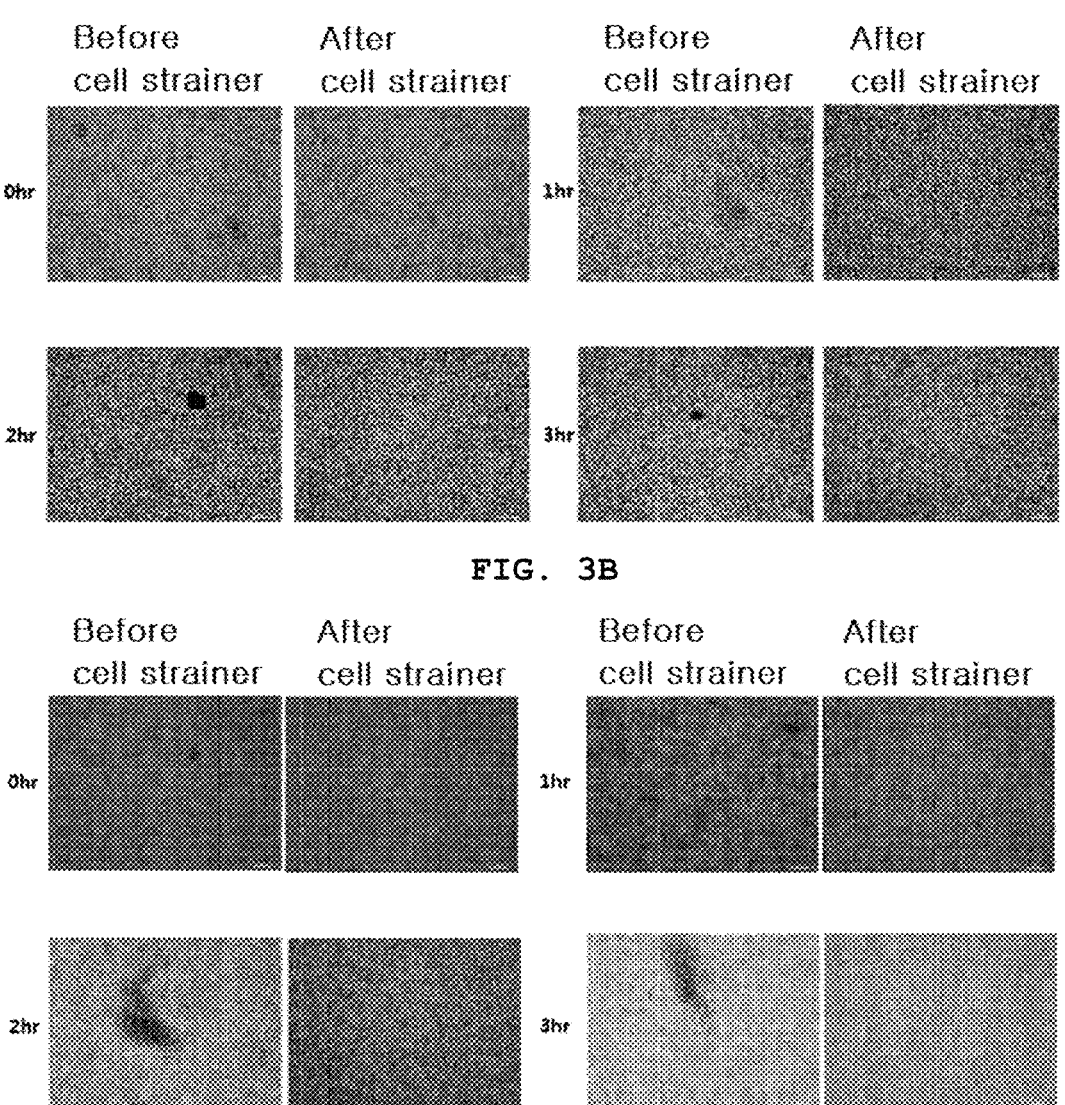
FIG. 3A is photographs illustrating microscopic observation results before and after untransformed cells passed through the cell strainer over time, respectively.
FIG. 3B is photographs illustrating microscopic observation results before and after transformed cells passed through the cell strainer over time, respectively.

According to the results, as shown in FIG. 3A, it was observed under a microscope that, after application of the 200 μm cell strainer at 0 hour, the cell aggregate was removed. Further, it was also observed under a microscope that the cell aggregates was no longer generated even after 3 hours has elapsed.

On the other hand, when the cell strainer was not applied, it was observed under a microscope that irregular and large aggregates remained without being removed. Furthermore, the agglomerates still remained even after the time has elapsed.

3-2. Identification of Cell Aggregation in TC Cells Over Time after Application of Cell Strainer The present inventors have cultured TC cells and collect a cell suspension. Some cells were filled in a vial without application of a cell strainer and observated cell flocculation over time. The remaining cell suspension was sieved with a cell strainer having a pore size of 100 μm, and the cells were filled in the vial, followed by determining cell aggregation phenomenon over time.

In order to determine whether or not the cell aggregation phenomenon of TC cells depending upon the pore size of the cell strainer, after passing the cell suspension through the cell strainer to completely remove cell aggregate, whether or not the cell aggregate was reduced has been checked.

According to the results, as shown in FIG. 3B, it was observed under a microscope that, after application of the 100 μm cell strainer at 0 hour, the cell aggregate was removed. Further, it was also observed under a microscope that the cell aggregate was no longer generated even after 3 hours has elapsed.

On the other hand, as shown in FIG. 3B, when the cell strainer was not applied, it was observed under a microscope that irregular and large aggregates remained without being removed. Furthermore, the aggregates still remained even after the time has elapsed.

Example 4. Identification of Osteoarthritis Therapeutic Effects by Treatment Using Selected Mixed Cells in MIA Osteoarthritis Model 4-1. Confirmation of the Effect of Pain Relief The present inventors have intended to determine effectiveness of the mixed cell therapeutic agent according to the present invention by: administering the selected mixed cells having a specific size or less defined in Example 2, that is, the mixed cells, which include HC cells having a particle diameter $D_{90}$ of less than 300 μm and TC cells having a particle diameter $D_{90}$ of less than 200 μm in a ratio of 3:1, to a rat animal model with osteoarthritis induced by MIA administration; and comparing analgesic effects therein.

In other words, in order to examine therapeutic effects of the selected mixed cells, the present inventors have prepared an MIA-induced osteoarthritis animal model, and then treated the model with the selected mixed cells, in order to observe a change in pain.

First, 6-week-old male rats (SPARGUE-DAWLEY, 200 to 225 g, Nara Biotech, Korea) were used for animal modeling. Animal experiments were conducted under approval by Institutional Animal Care and Use Committee in Kolon Life Science (IACUC No. KLS IACUC 2013-04) and under the supervision of a veterinary surgeon.

In order to induce arthritis, 50 μl of MIA (monosodium iodoacetate, Sigma, USA) solution with a concentration of 60 mg/mL was administered into the joint cavity in the left knee of a rat using a 31 G syringe.

2 weeks after the MIA administration, objects with developed osteoarthritis were subjected to administration of a vehicle (CS-10) and the mixed cells, respectively, into the joint cavity in the left knees.

TABLE 3

| Group | Gender | Number of animals | Animal code | Dosage of MIA administration (mg/ knee) | Administered substance (50 μL/knee) |
|---|---|---|---|---|---|
| G1 | M | 6 | 1481-1486 | 3 | Vehicle (CS-10) |
| G2 | M | 6 | 1505-1510 | 3 | $2.8 \times 10^5$ cells |

Thereafter, von Frey filament test was performed. This test was conducted using 50% up & down threshold method which was established in 1980 by Dixon (Chaplan S R et al., Quantitative assessment of tactile allodynia in the rat paw, Journal of Neuroscience Methods, 1994, 53: 55-63; and Dixon W. J., Efficient analysis of experimental observations, Annual Reviews Pharmacology Toxicology, 1980, 20: 441-62). Using a total of nine (9) von Frey filaments with N values of 0.4, 0.6, 1, 2, 4, 6, 8, and 15 grams (g), respectively, pain response was examined and a threshold value was calculated according to predetermined patterns.

A certain period of time (0, 7, 14, 21, 28, 35, 42, 49 and 56 days) passing after the administration of the mixed cells and the control substance, von Frey-filament test values were measured.

Figure 4A:
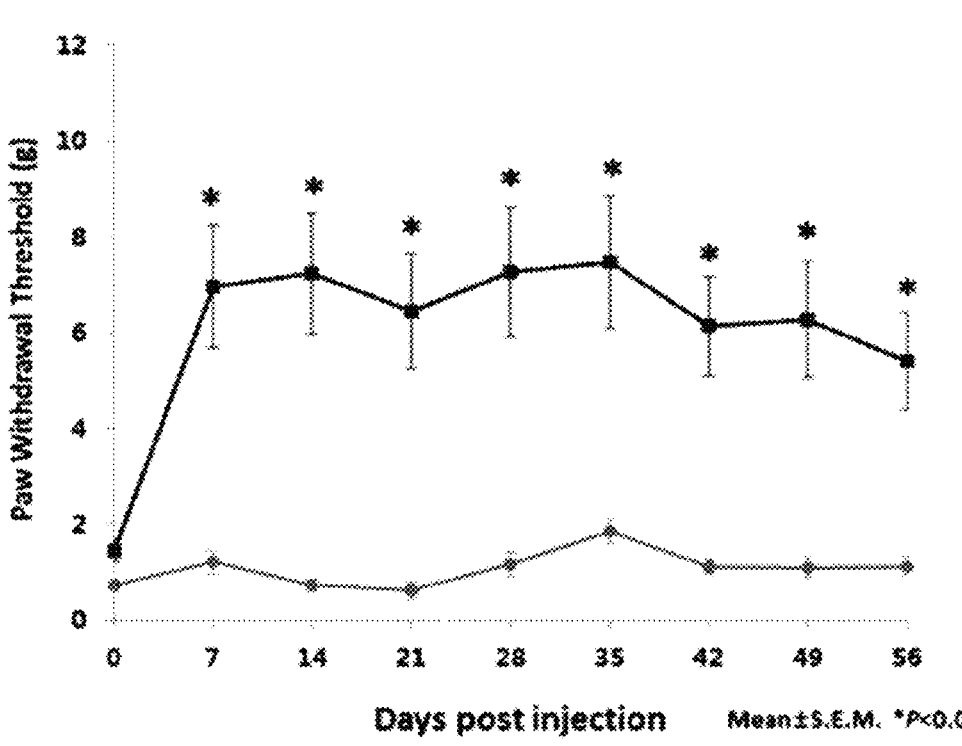
FIG. 4A is a graph illustrating results of von Frey filament tests when an MIA-induced osteoarthritis animal model was treated with the selected mixed cells.
Figure 4B:
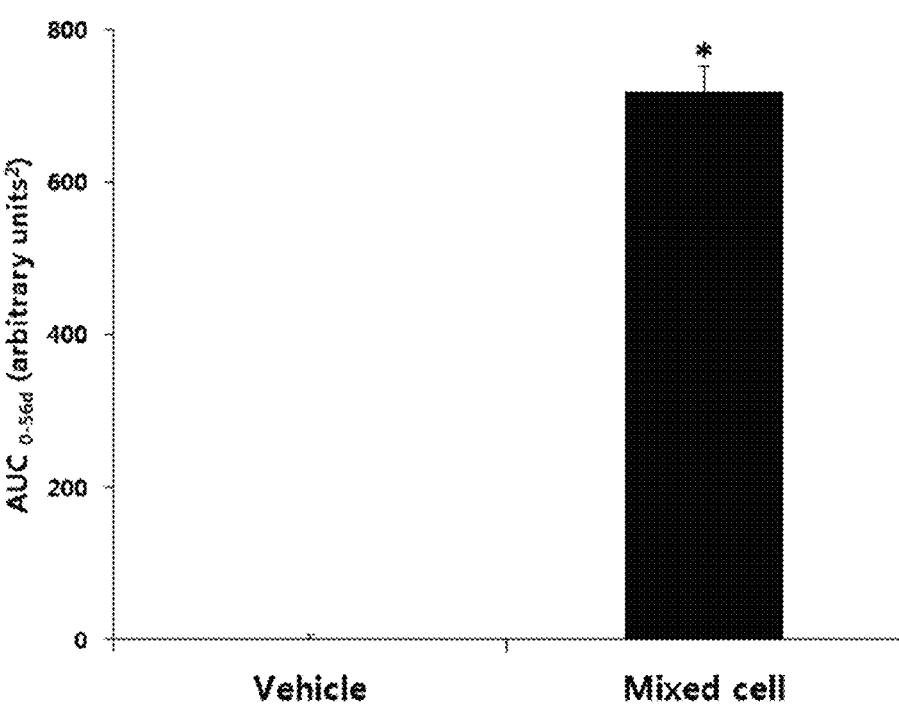
FIG. 4B a graph illustrating results of von Frey filament tests in an area under the curve (AUC) when treating the MIA-induced osteoarthritis animal model with the selected mixed cells.

According to the results, as shown in FIGS. 4A and 4B, the von Frey filament measurement values at the certain period of time (0, 7, 14, 21, 28, 35, 42, 49 and 56 days) after the administration of the mixed cells have demonstrated that the mixed cell administration group exhibited statistically significant analgesic effects, compared to the control group, that is, the CS-10 administration group ($p<0.05$). When these von Frey filament results were expressed as AUC value (area under the curve), which is used as a performance evaluation index, the mixed cell administration group showed statistically significant results, as compared to the control group, that is, the CS-10 administration group ($p<0.05$).

4-2. Identification of Cartilage Structural Improvement Effects

The present inventors have implemented comparison of cartilage structural improvement between a control group (vehicle) and the selected mixed cells having a specific size or less as prepared in Example 2, which were administered to a rat model with osteoarthritis induced by MIA administration, respectively, thereby determining effectiveness of the mixed cell therapeutic agent.

For this purpose, the animal model prepared as in Example 4-1 was sacrificed 56 days after the experiment, and then H & E staining analysis was implemented.

Figure 5:
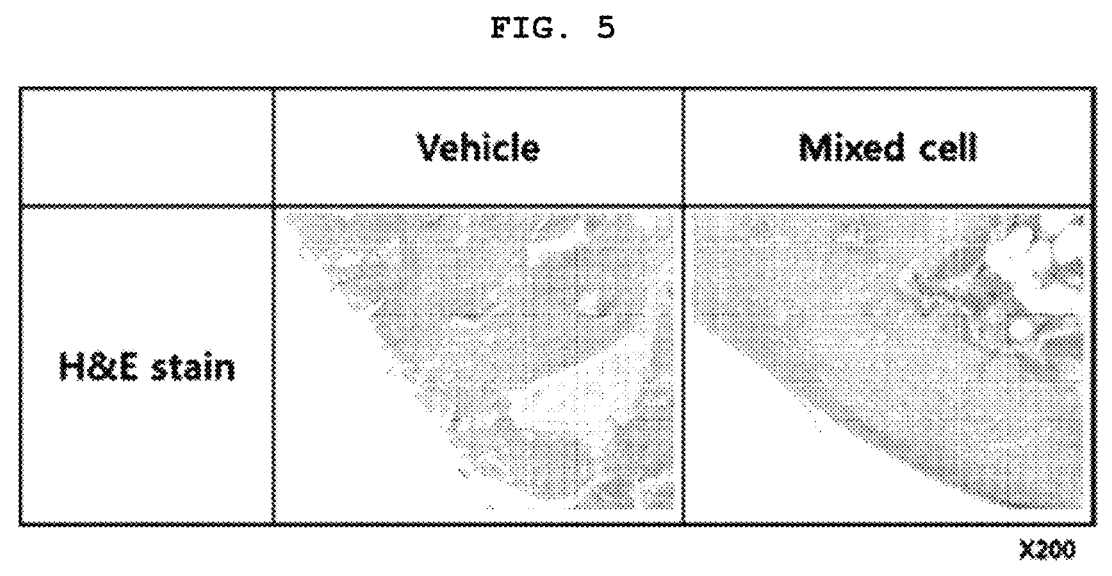

According to the result, as shown in FIG. 5, no cartilage structural improvement was observed in the control group (vehicle), that is, the CS-10 administration group, whereas cartilage structural improvement was observed in the mixed cell administration group.

Consequently, the mixed cells selected according to the present invention, wherein HC cells having a particle diameter $D_{90}$ of less than 300 μm and TC cells having a particle diameter $D_{90}$ of less than 200 μm are mixed in a ratio of 3:1, may exhibit excellent pain alleviation and cartilage formation effects even in the absence of aggregated cells. Therefore, the mixed cells may be used as an excellent therapeutic agent for osteoarthritis.

The invention claimed is:

1. A composition comprising:

a transformed mammalian cell population prepared by a process comprising collecting a cell suspension in which a transformed mammalian cell is cultured and sieving the cell suspension with a cell strainer having pore sizes ranging from 70 μm to less than 200 μm to remove any aggregate having a diameter larger than 70 μm to 200 μm, and an untransformed mammalian cell population prepared by collecting a cell suspension in which an untransformed mammalian cell is cultured and sieving the cell suspension with a cell strainer having pore sizes equal to or less than 300 μm to remove any aggregates having a diameter larger than 300 μm, wherein transformed mammalian cell population have a particle diameter D90 of less than 200 μm, and the untransformed mammalian cell population have a particle diameter D90 of less than 300 μm, wherein the transformed mammalian cell is transformed with a transforming growth factor beta (TGF-β) coding gene, and the untransformed mammalian cell is a chondrocyte or a chondroprogenitor cell; and the composition is intraarticular injectable.

2. The composition according to claim 1, wherein the preparing of the transformed mammalian cell population further comprises irradiating the transformed mammalian cell.

3. The composition according to claim 1, wherein the untransformed mammalian cell population and the transformed mammalian cell population are mixed in a mixing ratio of 1 to 10:1 based on the number of cells.

4. The composition of claim 1, further comprising a pharmaceutically acceptable carrier selected from the group consisting of lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrups, methylcellulose, methylhydroxybenzoate, propylhydroxybenzoate, talc, magnesium stearate, mineral oil, a lubricant, a wetting agent, a sweetening agent, a flavoring agent, an emulsifying agent, a suspending agent, a preservative, and a combination thereof.

5. The composition according to claim 1, wherein the untransformed mammalian cell population and the transformed mammalian cell population are mixed in a mixing ratio of 3:1 based on the number of cells.

6. A method for manufacturing an intraarticular injectable osteoarthritis therapeutic agent, comprising:

preparing a transformed mammalian cell population with TGF-β coding gene by collecting a cell suspension in which a mammalian cell transformed with TGF-β coding gene is cultured and sieving the cell suspension with a cell strainer having pore sizes equal to or less than 200 μm to obtain a filtrate of the transformed mammalian cell population;

preparing an untransformed mammalian cell population by collecting a cell suspension in which an untransformed mammalian cell is cultured and sieving the cell suspension with a cell strainer having pore sizes equal to or less than 300 μm to obtain a filtrate of the untransformed mammalian cell population;

mixing the filtrates of the transformed and untransformed mammalian cell populations.

7. The method according to claim 6, wherein the mixing comprises mixing the untransformed mammalian cell population and the transformed mammalian cell population in a mixing ratio of 1 to 10:1 based on the number of cells.

8. The method according to claim 6, wherein the preparing of the transformed mammalian cell population with TGF-β coding gene further comprises irradiating the transformed mammalian cell population.

9. The method of claim 6, further comprising adding to the mixed populations a pharmaceutically acceptable carrier selected from the group consisting of lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrups, methylcellulose, methylhydroxybenzoate, propylhydroxybenzoate, talc, magnesium stearate, mineral oil, a lubricant, a wetting agent, a sweetening agent, a flavoring agent, an emulsifying agent, a suspending agent, a preservative, and a combination thereof.

10. The method according to claim 6, wherein the mixing comprises mixing the untransformed mammalian cell population and the transformed mammalian cell population in a mixing ratio of 3:1 based on the number of cells.

11. A method for preparing an intraarticular injectable composition, the method comprising:

preparing a transformed mammalian cell population by collecting a cell suspension in which a transformed mammalian cell is cultured and sieving the cell suspension with a cell strainer having pore sizes equal to or less than 200 μm to obtain a filtrate of the transformed mammalian cell population;

preparing an untransformed mammalian cell population by collecting a cell suspension in which an untransformed mammalian cell is cultured and sieving the cell suspension with a cell strainer having pore sizes equal to or less than 300 μm to obtain a filtrate of the untransformed mammalian cell population; and mixing the filtrates of the transformed and untransformed mammalian cell populations.

12. The method of claim 11, wherein the untransformed mammalian cell population and the transformed mammalian cell population are mixed in a mixing ratio of 1 to 10:1 based on the number of cells.

13. The method of claim 11, wherein the untransformed mammalian cell population and the transformed mammalian cell population are mixed in a mixing ratio of 1 to 3:1 based on the number of cells.

14. The method of claim 11, wherein the transformed mammalian cell is a cell transformed with a transforming growth factor beta (TGF-β) coding gene; and the untransformed mammalian cell is a chondrocyte or a chondroprogenitor cell.

15. The method of claim 11, further comprising adding to the mixed populations a pharmaceutically acceptable carrier selected from the group consisting of lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrups, methylcellulose, methylhydroxybenzoate, propylhydroxybenzoate, talc, magnesium stearate, mineral oil, a lubricant, a wetting agent, a sweetening agent, a flavoring agent, an emulsifying agent, a suspending agent, a preservative, and a combination thereof.

16. A method for treating osteoarthritis, the method comprising administering the intraarticular injectable composition of claim 1 to a subject in need thereof.

* * * * *